United States Patent [19]

Yu et al.

[11] Patent Number: 5,871,729
[45] Date of Patent: Feb. 16, 1999

[54] SUPEROXIDE DISMUTASE-4

[75] Inventors: Guo-Liang Yu, Darnestown; Craig A. Rosen, Laytonsville; Claire M. Fraser, Queenstown; Jeannine D. Gocayne, Silver Spring, all of Md.

[73] Assignee: Human Genome Sciences, Inc., Rockville, Md.

[21] Appl. No.: 722,050

[22] PCT Filed: May 31, 1994

[86] PCT No.: PCT/US94/06099

§ 371 Date: Jan. 23, 1997

§ 102(e) Date: Jan. 23, 1997

[87] PCT Pub. No.: WO95/27781

PCT Pub. Date: Oct. 19, 1995

Related U.S. Application Data

[63] Continuation-in-part of Ser. No. 225,757, Apr. 11, 1994, Pat. No. 5,506,133.

[51] Int. Cl.$^6$ .............................. A61K 38/44; C12N 9/02
[52] U.S. Cl. .......................................... 424/94.4; 435/189
[58] Field of Search ............................ 424/94.4; 435/189

[56] References Cited

U.S. PATENT DOCUMENTS

| | | | |
|---|---|---|---|
| 4,976,959 | 12/1990 | Berger et al. | 424/94.2 |
| 5,238,837 | 8/1993 | Inoue et al. | 435/189 |
| 5,242,794 | 9/1993 | Whiteley et al. | 435/6 |
| 5,248,603 | 9/1993 | Marklund et al. | 435/189 |
| 5,252,476 | 10/1993 | Hallewell et al. | 435/189 |
| 5,360,729 | 11/1994 | Bartfeld et al. | 435/189 |
| 5,360,914 | 11/1994 | Inoue et al. | 548/546 |
| 5,455,029 | 10/1995 | Hartman et al. | 424/94.4 |
| 5,506,133 | 4/1996 | Yu et al. | 435/365 |
| 5,589,371 | 12/1996 | Heckl et al. | 435/189 |

FOREIGN PATENT DOCUMENTS

| | | |
|---|---|---|
| 0 499 621 B1 | 8/1992 | European Pat. Off. . |
| 62-103026 | 5/1987 | Japan . |
| 63-77822 | 4/1988 | Japan . |
| 63-313581 | 12/1988 | Japan . |
| 2-156884 | 6/1990 | Japan . |
| 4-108379 | 4/1992 | Japan . |
| 4-248984 | 9/1992 | Japan . |
| 4-312533 | 11/1992 | Japan . |
| 4-327541 | 11/1992 | Japan . |
| WO 91/06634 | 5/1991 | WIPO . |

OTHER PUBLICATIONS

Boissinot, M. et al., "Rational Design and Expression of a Heparin–Targeted Human Superoxide Dismutase," *Biochem. Biophys. Res. Comm.* 190(1):250–256 (1993).

Church, S.L., "Manganese superoxide dismutase: nucleotide and deduced amino acid sequence of a cDNA encoding a new human transcript," *Biochim. Biophys. Acta* 1087:250–252 (1990).

Danciger, E. et al., "Human Cu/Zn superoxide dismutase gene family: Molecular structure and characterization of four Cu/Zn superoxide dismutase–related pseudogenes," *Proc. Natl. Acad. Sci .USA* 83:3619–3623 (1986).

Deng, H.–X. et al., "Amyotrophic Lateral Sclerosis and Structural Defects in Cu,Zn Superoxide Dismutase," *Science* 261:1047–1051 (1993).

Hagiwara, H. et al., "Recombinant manufacture of human superoxide dismutase (h–SOD) derivatives," *Chem. Abstracts* 114(7):548 abstract No. 60461h (1991).

Inoue, M. et al., "Long chain carboxylic acid malemides for modification of superoxide dismutase," *Chem. Abstracts* 118(3):309 Abstract No. 18538w (1993).

Katsukura, Y. and H. Ochi, "Superoxide dismutase, its manufacture with Streptococcus and therapeutic use," *Chem. Abstracts* 107(25):633 Abstract No. 234823a (1987).

Kong, X.–J. et al., "Cu,Zn superoxide dismutase in vascular cells: changes during cell cycling and exposure to hyperoxia," *Am. J. Physiol.* 264:L365–L375 (1993).

Matsuyama, T. et al., "Pharmaceuticals for treatment of cerebral ischemia," *Chem. Abstracts* 118(8):462 Abstract No. 66893e (1993).

Otsu, N. et al., "Recombinant superoxide dismutase, its manufacture with *Escherichia coli*, and its use in vivo or in vitro to improve oxygen function," *Chem. Abstracts* 110(3):62 Abstract No. 18553g (1989).

Parge, H.E. et al., "Atomic structures of wild–type and thermostable mutant recombinant human Cu,Zn superoxide dismutase," *Proc. Natl. Acad. Sci. USA* 89:6109–6113 (1992).

Sakamoto, A. et al., "Nucleotide sequences of two cDNS clones encoding different Cu/Zn–superoxide dismutases expressed in developing rice seed (*Oryza sativa*L.)," *Plant Mol. Biol.* 19:323–327 (1992).

Suzuki, M., "Pharmaceuticals for control of transplant rejection," *Chem. Abstracts* 118(10):456 Abstract No. 87658x (1993).

Ueno, H. et al., "Modified superoxide dismutase as inflammation inhibitor and others," *Chem. Abstracts* 111(15):353 Abstract No. 129816k (1989).

European Search Report for EP 94 92 3172, mailed Oct. 20, 1997.

International Search Report for International application No. PCT/US94/06099, mailed Oct. 21, 1994.

English Language Abstract of JP–4–108379, Derwent World Patents Index, WPI Accession No. 92–171645/199221.

Baret et al., in Oxy Radicals and Their Scavenger Systems, vol. II: Cellular and Medical Aspects, Proc. 3rd Intl Conf. Superoxide & Superoxide Dismutase, Greenwald and Cohen (eds.) pp. 274–280, 1982.

(List continued on next page.)

*Primary Examiner*—Eric Grimes
*Attorney, Agent, or Firm*—Sterne, Kessler, Goldstein & Fox P.L.L.C.

[57] ABSTRACT

Polynucleotides which encode the polypeptide SOD-4, as well as such polypeptides, and antibodies against the polypeptide and the use of the polypeptide as a pharmaceutical for treating cerebral ischaemia, ulcers, inflammation, arrhythmia, oedema and paraquat intoxication as well as rheumatoid arthritis, osteoarthritis and radiation injury.

6 Claims, 4 Drawing Sheets

OTHER PUBLICATIONS

Rosen et al. "Mutations in Cu/Zn Superoxide Dismutase Gene Are Associated With Familia 1 Amyotrophic Lateral Sclerosis", *Nature, 362:*59–62 (Mar. 1993).

Baum et al. "Isolation And Characterization Of The Cystolic And Mitochondrial Superoxide Dismutase of Maize", *Arch. Biochem. Biophys., 206(2):*249–264 (Feb. 1981).

Hatanaka et al. "Preparation Of Superoxide Dismutase (SOD) Containing Heparin–Binding Site For Protease Resistance", *Chemical Abstracts, 117:*166676;(1992).

Cannon et al. "Two cDNAs Encode Two Nearly Identical Cu/Zn Superoxide Dismutase Proteins In Maize", *Mol. Gen. Genet, 219:*1–8 (1989).

Lee et al. "Generation of cDNA Probes Directed By Amino Acid Sequence: Cloning of Urate Oxidase", *Science, 239:*1288–1291 (1988).

```
   1 CTGGTTGGTGCTCCTGCGCCGGAGGAGTTCTGCGTCTCGGGGTGGTGACTGGGTCCAGAA   60
  61 TGGCTTCGGATTGGGGAACaGGGGACCCTCTGCACGTTGGAGTTCGCGGTGCAGATGACC  120
                                                               M  T

121 TGTCAGAGCTGTGTGGACGCGGTGCGCAAATCCCTGCAAGGGGTGGCAGGTGTCCAGGAT  180
     C  Q  S  C  V  D  A  V  R  K  S  L  Q  G  V  A  G  V  Q  D

181 GTGGAGGTGCACTTGGAGGACCAGATGGTCTTGGTACACACCACTCTACCCAGCCAGGAG  240
     V  E  V  H  L  E  D  Q  M  V  L  V  H  T  T  L  P  S  Q  E

241 GTGCAGGCTCTCCTGGAAGGCACGGGGCGGCAGGCGGTACTCAAGGGCATGGGCAGCGGC  300
     V  Q  A  L  L  E  G  T  G  R  Q  A  V  L  K  G  M  G  S  G

301 CAGTTGCAGAATCTGGGGGCAGCAGTGGCCATCCTGGGGGGGGCTGGCACCGTGCAGGGG  360
     Q  L  Q  N  L  G  A  A  V  A  I  L  G  G  A  G  T  V  Q  G

361 GTGgTGCGCTTCCTACAGcTGACCCcTGAGCGCTGCcTCATCGAGGGAAcTATTGACGGC  420
     V  V  R  F  L  Q  L  T  P  E  R  C  L  I  E  G  T  I  D  G

421 CTGGAGCCTGGGCTGCATGGACTCCACGTCCATCAGTACGGGGACCTTACAAACAACTGC  480
     L  E  P  G  L  H  G  L  H  V  H  Q  Y  G  D  L  T  N  N  C

481 AACAGCTGTGGGAATCACTTTAACCCTGATGGAGCATCTCATGGGGGCCCCCAGGACTCT  540
     N  S  C  G  N  H  F  N  P  D  G  A  S  H  G  G  P  Q  D  S

541 GACCGGCACCGcGGAGACCTGGGCAATGTCCGTGCTGATGCTGACGGCCGCGCCATCTTC  600
     D  R  H  R  G  D  L  G  N  V  R  A  D  A  D  G  R  A  I  F

601 AGAATGGAGGATGAGCAGCTGAAGGTGTGGGATGTGATTGCCCGCAGCCTGATTATTGAT  660
     R  M  E  D  E  Q  L  K  V  W  D  V  I  A  R  S  L  I  I  D

661 GAGGGAGAAGATGACCTGGGCCGGGGAGGCCATCCCTTATCCAAGATCACAGGGAACTCC  720
     E  G  E  D  D  L  G  R  G  G  H  P  L  S  K  I  T  G  N  S

721 GGGGAGAGGTTGGCCTGTGGCATCATTGCACGCTCCGCTGGCCTTTTCCAGAACCCCAAG  780
     G  E  R  L  A  C  G  I  I  A  R  S  A  G  L  F  Q  N  P  K

781 CAGATCTGCTCTTGCGATGGCCTCACCATCTGGGAGGAGCGAGGCCGGCCCATCGCTGGC  840
     Q  I  C  S  C  D  G  L  T  I  W  E  E  R  G  R  P  I  A  G

841 AAGGGCCGAAAGGAGTCAGCGCAGCCCCCTGCCCACCTTTGAGCAGGACCTCACCTTGGC  900
     K  G  R  K  E  S  A  Q  P  P  A  H  L

901 TCTGTTGCTGTCCTCCAGGGCGAGCACTTTCCACTTCCAGAGGGGGCCAGAGGGACTTTG   960
 961 CCTGCCCAGTCTTTGGAGAGCTCAGTACAGGGCAGGAGCTGCTGTGGTGTTCCCTTGGCA  1020
1021 AATGAAAGTTTTATTTTCGTTTGGGAAAAAAAAAAAAAAAAAAAAAAAAAAAAAAAAAA   1080
```

FIG. 1

```
              1         10        20        30        40        50        60        70        80
Human SOD4    GAAVAILGGAGTVQGVVRFLQLTPE.RCLIEGTIDGLEPGLHGLHVHQYGDLTNNCNSCGNHFNPDGASHGGPQDSDRHR
Schistosome   MK--CVMT-TAG-K---K-T-E-DNGPVHVHAEFS--KA-K-F---EF--T--G-T-A-A----TKQE--A-E--I--V
Bovine        TK--CV-K-D-P-Q-TIH-EAKG.D.TVVT-S-T--TE-D--F----F---N-QG-T-A-P----LSKK---K-EE--V
Cauliflower   AKG-CV-NSSEG-K-TIF-THEGNG.ATTVT--VS--R----F----AL--N-G-M-T-P-----KT--A-E-AN--A
Drosophila    VK--CVIN...DAK-T-F-E-ESSGTPVKVS-EVC--AK----F----EF--N-G-M-S-P---Y-KE--A-V-EN--L
Human SOD1    TK--CV-K-D-P---IIN-E-KESNGPVKVW-S-K--TE----F----EF--N-AG-T-A-P----LSRK---K-EE--V
Tomato        VK--CV-NSSEG-S-TYL-T-VGVA.PTTVN-N-S--K-----F----AL--N-G-M-T-P-Y--A-KE--A-E-EV--V
Maize         VK---V-A-TD..K-TIF-S-EGDG.PTTVT-S-S--K-----F----AL--T-G-M-T-P----V-KE--A-E-E---A
Mouse         MK--CV-K-D-P---TIH-E-KASG.EPWLS-Q-T--TE-Q--F-----N-QG-T-A-P----HSKK---A-EE--V
Xenopus       VK--CV-A-S-D-K---R-E-QDDG.DVTV--K-E--TD-N--F-I-VF--N--G-L-A-P---QNKN--S-K-A---V
S. cerevisiae VQ--AV-K-DAG-S---K-E-ASESEPTTVSYE-A-NS-NAERF-I-EF--A--G-V-A-P---FKKT--A-T-EV--V 81        90        100       110       120       130       140       150
Human SOD4    GDLGNVRADADGRAIFRMEDEQLKVWD...VIARSLIIDEGEDDLGRGGHPLSKITGNSGERLACGIIARSAG
Schistosome   ----V-G---N-VYNAT-KLISLNGSHSI-G--MV-H-N------E----V---A-G-----VVGLA-E
Bovine        ----T--KN-V---VDIV-PLISLSGEYSI-G-TMVVH-KP-----NEE-TK---A-S-----V-GIIK.
Cauliflower   ----IIVGD--T-T-TIT-S-IPLSGPNSIVG-AIVVHADP----K---E---LS---A-G-V-----GIQG.
Drosophila    ----IE-TG-CPTKVNIT-SKITLFGADSI-G-TVVVHADA----Q---E---S---A-A-IG--V-GIIKV
Human SOD1    ----T--K--V-DVSI--SVISLSGDHCI-G-T--VVH-KA----K--NEE-TK---A-S-----V-GIIQ.
Tomato        ----ITVGE--T-S-TIT-K-IPLTGPQSI-G-AVVVHADP----K---E---S---A-G-I----GIQG.
Maize         ----T-GE--VVNVNIT-S-IPLAGPHSI-G-AVVVHADP----K---E---S---A-G-V-----GIQG.
Mouse         ----T-GK--V-NVSI--RVISLSGEHSI-G-TMVVH-KQ----K--NEE-TK---A-S-----V-GIIQ.
Xenopus       ----T.E.G-V-Q-NFT-P-ISLKGERSI-G-TAVVH-KQ----K---K--DDE-LK---A-G-----V-GFCP.
S. cerevisiae --M---KT-EN-V-KGSFK-SLI-LIGPTS-VG--VV-HA-Q----K-DTEE-LK----A-P---VIGITN.
```

FIG.2

SUPEROXIDE DISMUTASE-4

This application is a continuation-in-part of U.S. application Ser. No. 08/225,757 filed Apr. 11, 1994 now U.S. Pat. No. 5,506,133.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Superoxide Dismutase-4 (SOD-4).

There is a very strong thermodynamic driving force for the reactions between oxygen and biochemical compounds in the body such as proteins, carbohydrates, lipids and nucleic acids. If such reactions go to completion, water, carbon dioxide and a number of waste products are formed as end products with the release of large amounts of energy. Oxidation of biological compounds is the source of energy of living organisms. Such reactions occur spontaneously but are very slow due to reaction barriers. These barriers are overcome by enzymes in intermediary metabolism, and the final reaction with oxygen takes place in the mitochondria, where the oxygen is reduced by four electrons to water without the liberation of any intermediate products. The reaction is accomplished by cytochrome oxidase complex in the electron transport chain and the energy is bound by the formation of ATP.

However, the direct four step reduction of oxygen to water is unique, and when oxygen reacts spontaneously or is catalyzed by enzymes it is forced to react one step at a time. A series of reactive and toxic intermediates are formed, namely the superoxide radical ($O_2^-$), hydrogen peroxide ($H_2O_2$), and the hydroxyl radical ($OH^-$).

Two of these, $O_2^-$ and $OH^-$, have single unpaired electrons and are therefore called free radicals. A few percent of the oxygen consumption in the body has been estimated to lead to the formation of the toxic reduction intermediates. The toxic affects of oxygen are mainly ascribable to the actions of these intermediates.

Oxygen in itself reacts slowly with most biochemical compounds. The toxic reactions are in general initiated by processes giving rise to oxygen radicals, which in themselves cause direct damage to biochemical compounds or start chain reactions involving oxygen.

Some compounds react spontaneously with oxygen, i.e., they autoxidize. Virtually all autoxidations result in the formation of toxic oxygen reduction intermediates. Autoxidation of adrenalin, pyrogallol and several other compounds lead to the formation of the superoxide radical. When ionizing radiation passes through an aqueous solution containing oxygen, the superoxide radical is the radical found in the highest concentration. The toxic oxygen reduction products so formed are of fundamental importance for the killing ability of the cells, but may also lead to damage in the surrounding tissue.

Hydrogen peroxide is always formed when superoxide is formed by way of the dismutation reaction. Most oxidases in the body directly reduce oxygen to hydrogen peroxide.

Organisms living in the presence of oxygen have been forced to develop a number of protective mechanisms against the toxic oxygen reduction metabolites. The protective factors include superoxide dismutases (SOD) which dismutate the superoxide radical and are found in relatively constant amounts in mammalian cells and tissue. The best known of these enzymes is CuZnSOD which is a dimer with a molecular weight of 33,000 containing two copper and two zinc atoms. CuZnSOD is found in the cytosol and in the intermembrane space of the mitochondria. MnSOD is a tetramer with a molecular weight of 85,000 containing four Mn atoms, and is mainly located in the mitochondrial matrix. Until recently the extra cellular fluids were assumed to lack SOD activity. However U.S. Pat. No. 5,248,603 recently disclosed the presence of a superoxide dismutase in extracellular fluids (e.g., blood plasma, lymph, synovial fluid and cerebrospinal fluid) which was termed EC-SOD.

Crystallographic structures of recombinant human CuZnSOD have been determined, refined and analyzed at 2.5 A resolution for wild-type and a designed thermal stable double-mutant enzyme (Cys-6—Ala, Cys-111—Ser). There is a helix dipole interaction with a Zn site, and 14 residues form two or more structurally conserved side-chain to main-chain hydrogen bonds that appear critical to active-site architecture, loop confirmation and the increased stability resulting from the Cys-111—Ser mutation. Parge, H. E. et al, Proc. Natl. Acad. Sci. U.S.A., 89:6109–13 (1992).

Mutations in the CuZnSOD gene occur in patients with the fatal neurodegenerative disorder familial amyotrophic lateral sclerosis. Screening of the CuZnSOD coding region revealed that the mutation Ala 4 to Val in exon 1 was the most frequent one, mutations were identified in exons 2, 4 and 5 but not in the active site region formed by exon 3. Thus, defective CuZnSOD is linked to motor neuron death and carries implications for understanding and possible treatment of familial amyotrophic lateral sclerosis. The polypeptide of the present invention, SOD-4, is structurally and functionally related to CuZnSOD.

Japanese Patent No. 4327541 discloses a therapeutic drug for immuno-reactions with organs after transplantation containing the active substance of human CuZnSOD obtained by gene recombination.

Japanese Patent No. 4312533 discloses a composition for treating cerebral ischaemia which comprises recombinant Cuzn human SOD and inhibits delayed nerve necrosis accompanying is chaemia.

Japanese Patent No. 4248984 discloses a superoxide dismutase derivative which has a longer half-life in blood than SOD and therefore helps treat various diseases.

European Patent No. 499621 discloses a method for purifying recombinant CuZnSOD and a method for increasing the yield of the B isoform analog of this polypeptide.

Japanese Patent No. 2156884 discloses a 153 amino acid polypeptide having human superoxide dismutase properties and a DNA sequence encoding such polypeptide, a DNA sequence expressed by the nucleic acid sequence and production of the polypeptide by culture of host cells.

Japanese Patent No. 63313581. discloses a pharmacologically active modified superoxide dismutase which is obtained by reacting SOD with a compound containing an amino or carboxyl group.

Japanese Patent No. 63077822 discloses an agent for improving the function of organs which uses a human SOD-like polypeptide as the active substance.

In accordance with one aspect of the present invention, there is provided a novel mature polypeptide which is SOD-4, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, for treating inflammatory pathologies, ulcers, arrhythmia, ischaemia, oedema, paraquat intoxication, rheumatoid arthritis and osteoarthritis, reducing reperfusion injuries and decreasing blood pressure.

In accordance with yet a further aspect of the present invention, there is provided an antibody against such polypeptides. These and other aspects of the present invention should be apparent to those skilled in the art from the teachings herein.

The following drawings are illustrative of embodiments of the invention and are not meant to limit the scope of the invention as encompassed by the claims.

FIG. 1 shows the cDNA sequence (SEQ ID NO:1) and deduced amino acid sequence for the (SEQ ID NO:2) SOD-4 gene. The amino acid sequence encodes for one of the mature forms of the polypeptide, since there are at least two in-frame ATG start codons. The mature polypeptide could start at either one of the ATG codons. The standard one letter abbreviation for amino acids is used.

FIG. 2 displays the amino acid homology between SOD-4 (SEQ ID NO:2) with eleven other cytosolic CuZn-SODs from various species. Schistosome (SEQ ID NO:3), Bovine (SEQ ID NO:4), Cauliflower (SEQ ID NO:5), Drophila (SEQ ID NO:6), Human SOD1 (SEQ ID NO:7), Tomato (SEQ ID NO:8), Maize (SEQ ID NO:9), Mouse (SEQ ID NO:10), Xenopus (SEQ ID NO:11), and S. cerevisiae (SEQ ID NO:12). The copper-zinc-bind-sites (in boldface type) are formed by six His residues and one Asp residue. The Arg (R) residue is believed necessary to guide the superoxide to the activity site. Identical residues are represented by dashes and deletions are represented by dots.

Figure 3:
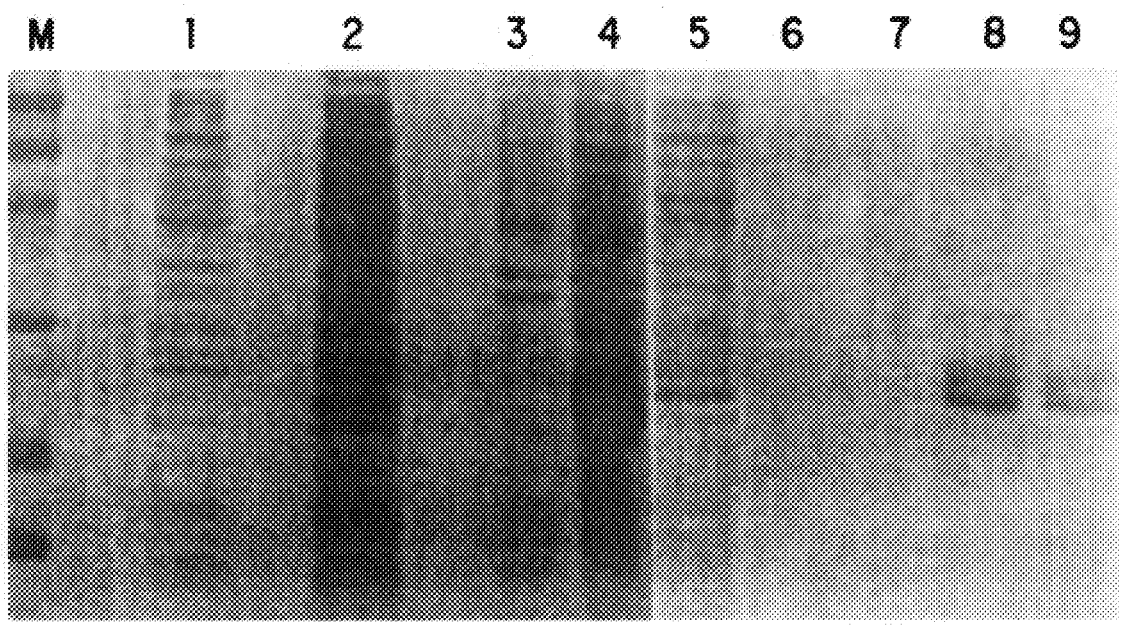
FIG. 3 shows the results of bacterial expression and purification of human SOD-4 after separation on an SDS polyacrylamide gel.

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 75716 on Mar. 22, 1994.

The polynucleotide of the present invention was isolated from an early stage human brain cDNA library. It contains an open reading frame encoding a polypeptide of 255 amino acids. The polypeptide has the highest degree of homology to CuZnSOD isolated from *Schistosoma mansoni* having 51% identity and 72% similarity over a 151 amino acid overlap.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same, mature polypeptide as the DNA of FIG. 1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pD10 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term stringent conditions, means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a SOD-4 polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered, (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the SOD-4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomvces, Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pRK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232–8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the pblypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatogradhy hydroxylapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

SOD-4 may also be employed as an anti-inflammatory agent. Other SOD proteins have been shown to exhibit an anti-inflammatory affect in a series of animal models of inflammation as well as in inflammatory diseases in animals (Huber et al, eds. Michelson el al, Academic Press, 517–549, (1977). SOD-4 may also be used to treat rheumatoid arthritis and the adverse effects of ionizing radiation since, in humans, positive affects have been shown using SOD proteins to treat rheumatoid arthritis and arthroses as well as adverse affects of treatment with ionizing radiation. The mechanism by which SOD-4 works is by removing oxidation products, which products cause tissue degeneration.

SOD-4 may be used to treat Crohn's disease, Bechet's disease, dermatitis, ulcers, ulcerative colitis, and against the adverse effects of radiation therapy. Other SOD proteins have been found to be effective against these conditions (Niwa, Y et al, Free Rad. Res. Comms. 1:137–153 (1985)).

If the supply of blood to a tissue is cut off, the tissue will slowly become necrotic. Oxygen radicals formed as a result of the reappearance of oxygen in previously ischaemic tissue appear to contribute to the damage. Thus the removal of these free radicals by SOD-4 helps to protect tissue against damage. SOD-4 may be employed to reduce the incidence of ischaemia and reperfusion induced arrhythmias by a similar mechanism, since SOD proteins have been reported to affect these conditions (Woodward, B. et al, J. Mol. Cell. Cardiol. 17:485–493 (1985). In the same manner, SOD-4 may be employed to treat cerebral ischaemia and kidney ischaemia, SOD proteins have been demonstrated to protect tissues in ischaemia or anoxiareperfusion models in the kidney (Baker, G. L., et al., Am. Surg., 202:628–41 (1985).

Also, SOD-4 may be employed in connection with kidney transplantations and other organ transplantations such as skin, lung, liver and pancreas.

SOD-4 may be employed to treat burns. The local oedema after an experimental slight burn in rats could be somewhat decreased through injection of SOD proteins (Bjork and Artursson, Burns, 9:249–256 (1983).

Parenterally administered CuZnSOD has been reported to prevent bronchopulmonary dysplasia in preterm neonates suffering from infantile respiratory distress. The CuZnSOD has recently received orphan drug status for this treatment. Accordingly, SOD-4 may also be employed to treat these diseases also. (Rosenfeld W. et al, J. Pediatr. 105:781–785 (1984).

In various types of autoimmune diseases, such as systemic lupus erythematosus, and rheumatoid arthritis an increased frequency of chromosomal breaks in lymphocytes has been demonstrated. Plasma from such patients contains a chromosome breaking factor, called clastogenic factor. Superoxide radicals in the plasma results in formation of this factor. SOD-4 may protect against this clastogenic activity by removing the superoxide radicals.

Superoxide radicals tend to damage cells, DNA and proteins by oxidative stress which may disrupt the normal cell cycle and lead to uncontrolled division of cells which is the basis of a cancer. Accordingly, SOD-4 can be employed to prevent or control cancer by the removal of superoxide radicals from a patient's system.

Oxygen radicals contribute to the damaging affects of a number of toxic substances such as paraquat and alloxan. SOD-4 may protect against these toxic substances through direct injection.

Alloxan has been reported to have diabetogenic activity. SOD-4 may protect against this diabetogenic activity of alloxan in vivo. Beta-cells of the pancreas are extremely sensitive to alloxan, and this sensitivity may lead to insulin-dependent diabetes mellitus. It may therefore be contemplated to protect the Beta cells with injections with SOD-4 at the first onset of diabetes mellitus.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The amounts and dosage regimens of SOD-4 administered to a subject will depend on a number of factors such as the mode of administration, the nature of the condition being treated and the judgment of the prescribing physician. Generally speaking, they are given, for example, in therapeutically effective doses of at least about 10 $\mu$g/kg body weight and in most cases they will be administered in an amount not in excess of about 8 mg/Kg body weight per day and preferably the dosage is from about 10 $\mu$g/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

In accordance with a further aspect of the present invention, there is provided a process for determining susceptibility to disorders directly related to a mutation in the SOD-4 gene product. Such disorders include but are not limited, amyotrophic lateral sclerosis "ALS", and Parkinson's disease. Thus, a mutation in an SOD-4 protein indicates a susceptibility to these disorders, and the nucleic acid sequences encoding an SOD-4 polypeptide may be employed in an assay for ascertaining such susceptibility. Thus, for example, the assay may be employed to determine a mutation in a human SOD-4 protein as herein described, such as a deletion, truncation, insertion, frameship, etc., with such mutation being indicative of a susceptibility to the above-mentioned diseases.

A mutation may be ascertained, for example, by a DNA sequencing assay. Tissue samples, including but not limited to blood samples, are obtained from a patient. The samples are processed by methods known in the art to capture the RNA. The first strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the SOD-4 polypeptide of the invention. The primer sequence is generally comprised of 15 to 30 and preferable from 18 to 25 consecutive basis of the SOD-4 gene. The primers are used in pairs (one "sense" and one "anti-sense") to amplify the cDNA from the patients by the PCR method such that three overlapping fragments of the patients' cDNAs are generated. The overlapping fragments are then subjected to dideoxynucleotide sequencing using a set of primer sequences synthesized to correspond to the base pairs of the cDNAs at a point approximately every 200 base pairs throughout the gene. The primer sequences are used for sequencing to determine where a mutation in the patients' SOD-4 protein may be. The sequence information determined from the patient is then compared to non-mutated sequences to determine if any mutations are present.

In another embodiment, the primer sequences are used in the PCR method to amplify a mutated region. The region could be sequenced and used as a diagnostic tool to predict a predisposition to such mutated genes.

Alternatively, the assay to detect mutations in the SOD-4 gene may be performed by generating cDNA from the RNA and expressing the protein encoded by the cDNA by in vitro transcription and translation. The expressed protein may then be analyzed by electrophoresis on an SDS, polyacrylamide or other gel. A "normal" SOD-4 gene product is also electrophoresed on the gel, and the gel is then dried and subjected to auto-radiography and the suspected mutated gene product and the "normal" gene product are analyzed and any differences in the banding pattern of such gene products are indicative of a mutation in the cDNA. A mutation in the gene product can also be detected by using SOD-4 antibody in a Western Blot analysis. Accordingly, the mutations in the genes of the present invention may be determined directly by sequencing or indirectly by examining an expressed protein.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A.., Virology, 52:456–457 (1973).

EXAMPLE 1

Bacterial Expression and Purification of SOD-4

The DNA sequence encoding for SOD-4, ATCC # 75716 is initially amplified using PCR oligonucleotide primers corresponding to the 5' and 3' sequences of the processed SOD-4 protein (minus the signal peptide sequence) and the vector sequences 3' to the SOD-4 gene. Additional nucleotides corresponding to SOD-4 are added to the 5' and 3' sequences respectively. The 5' oligonucleotide primer has the sequence 5'-CGGGATCCATGGGCAGCGGCCAGTTG-3' and (SEQ ID NO:13) contains a Bam HI restriction enzyme site followed by 18 nucleotides of SOD-4 coding sequence starting from one of the presumed terminal amino acids of the processed protein. The 3' sequence, 5'-CGTCTAGAGGTCCTGCTCAAAGGTGGG-3' (SEQ ID NO:14) contains complementary sequences to an Xba I restriction site and the last 21 nucleotides of SOD-4 and to a pD10 vector sequence located 3' to the SOD-4 DNA insert. The restriction enzyme sites correspond to the restriction enzyme sites on the bacterial expression vector pD10 (Qiagen, Inc. 9259 Eton Avenue, Chatsworth, Calif. 91311). pD10 encodes antibiotic resistance (Amp'), a bacterial origin of replication (ori), an IPTG-regulatable promoter operator. (P/O), a ribosome binding site (RBS), a 6-His tag and restriction enzyme sites. pD10 was then digested with Bam HI and Xba I. The amplified sequences were ligated into pD10 and were inserted in frame with the sequence encoding for the histidine tag and the RBS. The ligation mixture was then used to transform E. coli strain M15/rep4 available from Qiagen under the trademark M15/rep 4 by the procedure described in Sambrook, J et al., Molecular Cloning: A Laboratory Manual, Cold Spring Laboratory Press, 1989. M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 μg/ml) and Kan (25 μg/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized SOD-4 was purified from this solution by chromatography on a Nickel-Chelate column under conditions that allow for tight binding by proteins containing the 6-His tag. Hochuli, E. et al., J. Chromatography 411:177–184 (1984). Proteins from different stages of purification were separated on a 12.5% SDS polyacrylamide gel and stained with Coomassie blue dye. M represents a molecular sizing marker. Lanes 1 and 2 are total extracts from bacteria containing the vector pD10 in the absence (lane 1) and presence (lane 2) of IPTG. Lanes 3 and 4 are total extracts from bacteria containing the expression plasmid pD10-SOD-4 in the absence (lane 3) and presence (lane 4) of IPTG. Lanes 5 through 9 represent elution fractions from a Nickel-Chelate column. Lane 5 is flow-through; lanes 6 and 7 represent elution fractions washed with 6 M guanidine HCl, 50 mM $NaPO_4$, pH 8 and pH 6; lanes 8 and 9 are elution fractions washed with 6 M guanidine HCl 50 mM NaPO, pH 5 and pH 2. See FIG. 3.

EXAMPLE 2
Expression of Recombinant SOD-4 in COS cells

The expression of plasmid, pSOD-4-HA is -derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire SOD-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

Figure 4:
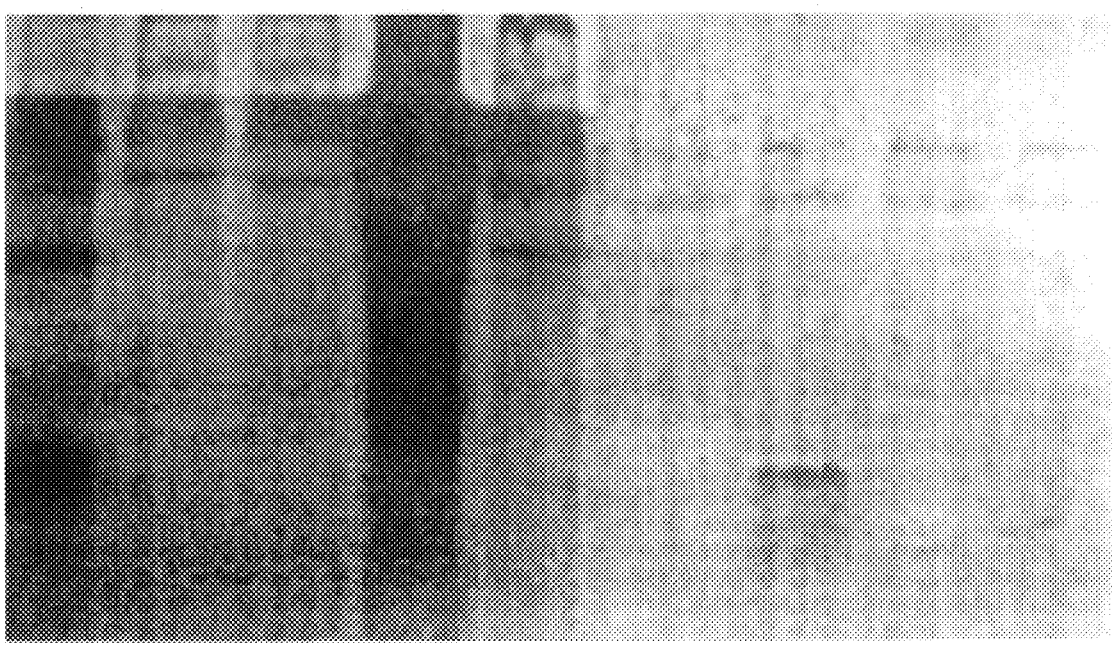
FIG. 4 shows the results of expression of recombinant SOD-4 in COS cells after separation on an SDS polyacrylamide gel.

The plasmid construction strategy is described as follows:

The DNA sequence encoding for SOD-4, ATCC # 75716 was constructed by PCR using two primers: the 5' primer sequence 5'-AATTAACCCTCACTAAAGGG-3' in (SEQ ID NO:15) pBluescript vector; the 3' sequence 5'-CGCTCTAGA- CAAGCGTAGCTGG-GACGTCGTATGGGTGGTGGGCA GGGGGCTG-3' (SEQ ID NO:16) contains complementary sequences to an Xba I restriction enzyme site, translation stop codon, HA tag and the last 18 nucleotides of the SOD-4 coding sequence (not including the stop codon). Therefore, the PCR product contains a Bam HI site from the pBluescript vector, SOD-4 coding sequence followed by HA tag fused in frame, a translation termination stop codon next to the HA tag, and an Xba I site. The PCR amplified DNA fragment and the vector, pbluescript, were digested with Bam HI and Xba I restriction enzymes and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant SOD-4, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the SOD-4-HA protein was detected by radiolabelling and immunoprecipitation method. (E. Harlow, D. Lane, Antibodies: A Laboratory Manual, Cold Spring Harbor Laboratory Press, (1988)). Proteins were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). $^{35}$S-cysteine labeled proteins from COS cell lysates and supernatants were immunoprecipitated with an HA polyclonal antibody and separated using 15% SDS-PAGE. M equals molecular weight markers. Lanes 1 through 4 are cell lysates. Lanes 5 through 8 are supernatants. Lanes 1 and 5 are mock controls with no DNA. Lanes 2 and 6 are MIP-1γ control for secreted proteins. Lanes 3 and 7 are control for cell lysate and lanes 4 and 8 are SOD-4. See FIG. 4.

Numerous modifications and variations of the present invention are possible in light of the above teachings and, therefore, within the scope of the appended claims, the invention may be practiced otherwise than as particularly described.

What is claimed is:

1. An isolated polypeptide selected from the group consisting of:
    (i) a SOD-4 polypeptide having the deduced amino acid sequence of amino acids 1 to 255 of FIG. 1 (SEQ ID NO:2) and fragments thereof;
    (ii) a SOD-4 polypeptide having the amino acid sequence of amino acids 2 to 255 of FIG. 1 (SEO ID NO:2) and fragments thereof; and
    (iii) a SOD-4 polypeptide encoded by the cDNA of ATCC Deposit No. 75716 and fragments thereof.

2. The polypeptide of claim 1 wherein the polypeptide is SOD-4 having the deduced amino acid sequence of amino acids I to 255 of FIG. 1 (SEQ ID NO:2).

3. The polypeptide of claim 1, wherein the polypeptide has the amino acid sequence of amino acids 2 to 255 of FIG. 1 (SEQ ID NO:2).

4. The polypeptide of claim 1, wherein the polypeptide has the amino acid sequence as encoded by the cDNA of ATCC Deposit No. 75716.

5. A pharmaceutical composition comprising the polypeptide of claim 1 and a pharmaceutically acceptable carrier.

6. A method for the treatment of a patient having need of SOD-4 comprising: administering to the patient a therapeutically effective amount of the polypeptide of claim 1.

* * * * *

UNITED STATES PATENT AND TRADEMARK OFFICE
CERTIFICATE OF CORRECTION

PATENT NO. : 5,871,729

DATED : February 16, 1999

INVENTOR(S) : Yu et al.

It is certified that error appears in the above-indentified patent and that said Letters Patent is hereby corrected as shown below:

At column 32, in claim 2, line 3, please delete "I" and insert therein --1--.

Signed and Sealed this

Twenty-third Day of November, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1080 base pairs
        ( B ) TYPE: nucleic acid
        ( C ) STRANDEDNESS: double
        ( D ) TOPOLOGY: linear ( i i ) MOLECULE TYPE: DNA (cDNA)

( i x ) FEATURE:
        ( A ) NAME/KEY: CDS
        ( B ) LOCATION: 115..879

( x i ) SEQUENCE DESCRIPTION: SEQ ID NO:1:

```
CTGGTTGGTG    CTCCTGCGCC    GGAGGAGTTC    TGCGTCTCGG    GGTGGTGACT    GGGTCCAGAA        6 0
```

```
TGGCTTCGGA TTGGGGAACA GGGGACCCTC TGCACGTTGG AGTTCGCGGT GCAG ATG                117
                                                             Met
                                                             1

ACC TGT CAG AGC TGT GTG GAC GCG GTG CGC AAA TCC CTG CAA GGG GTG                165
Thr Cys Gln Ser Cys Val Asp Ala Val Arg Lys Ser Leu Gln Gly Val
            5                   10                  15

GCA GGT GTC CAG GAT GTG GAG GTG CAC TTG GAG GAC CAG ATG GTC TTG                213
Ala Gly Val Gln Asp Val Glu Val His Leu Glu Asp Gln Met Val Leu
            20                  25                  30

GTA CAC ACC ACT CTA CCC AGC CAG GAG GTG CAG GCT CTC CTG GAA GGC                261
Val His Thr Thr Leu Pro Ser Gln Glu Val Gln Ala Leu Leu Glu Gly
        35                  40                  45

ACG GGG CGG CAG GCG GTA CTC AAG GGC ATG GGC AGC GGC CAG TTG CAG                309
Thr Gly Arg Gln Ala Val Leu Lys Gly Met Gly Ser Gly Gln Leu Gln
50                  55                  60                  65

AAT CTG GGG GCA GCA GTG GCC ATC CTG GGG GGG GCT GGC ACC GTG CAG                357
Asn Leu Gly Ala Ala Val Ala Ile Leu Gly Gly Ala Gly Thr Val Gln
                70                  75                  80

GGG GTG GTG CGC TTC CTA CAG CTG ACC CCT GAG CGC TGC CTC ATC GAG                405
Gly Val Val Arg Phe Leu Gln Leu Thr Pro Glu Arg Cys Leu Ile Glu
                85                  90                  95

GGA ACT ATT GAC GGC CTG GAG CCT GGG CTG CAT GGA CTC CAC GTC CAT                453
Gly Thr Ile Asp Gly Leu Glu Pro Gly Leu His Gly Leu His Val His
            100                 105                 110

CAG TAC GGG GAC CTT ACA AAC AAC TGC AAC AGC TGT GGG AAT CAC TTT                501
Gln Tyr Gly Asp Leu Thr Asn Asn Cys Asn Ser Cys Gly Asn His Phe
    115                 120                 125

AAC CCT GAT GGA GCA TCT CAT GGG GGC CCC CAG GAC TCT GAC CGG CAC                549
Asn Pro Asp Gly Ala Ser His Gly Gly Pro Gln Asp Ser Asp Arg His
130                 135                 140                 145

CGC GGA GAC CTG GGC AAT GTC CGT GCT GAT GCT GAC GGC CGC GCC ATC                597
Arg Gly Asp Leu Gly Asn Val Arg Ala Asp Ala Asp Gly Arg Ala Ile
                150                 155                 160

TTC AGA ATG GAG GAT GAG CAG CTG AAG GTG TGG GAT GTG ATT GCC CGC                645
Phe Arg Met Glu Asp Glu Gln Leu Lys Val Trp Asp Val Ile Ala Arg
                165                 170                 175

AGC CTG ATT ATT GAT GAG GGA GAA GAT GAC CTG GGC CGG GGA GGC CAT                693
Ser Leu Ile Ile Asp Glu Gly Glu Asp Asp Leu Gly Arg Gly Gly His
            180                 185                 190

CCC TTA TCC AAG ATC ACA GGG AAC TCC GGG GAG AGG TTG GCC TGT GGC                741
Pro Leu Ser Lys Ile Thr Gly Asn Ser Gly Glu Arg Leu Ala Cys Gly
        195                 200                 205

ATC ATT GCA CGC TCC GCT GGC CTT TTC CAG AAC CCC AAG CAG ATC TGC                789
Ile Ile Ala Arg Ser Ala Gly Leu Phe Gln Asn Pro Lys Gln Ile Cys
210                 215                 220                 225

TCT TGC GAT GGC CTC ACC ATC TGG GAG GAG CGA GGC CGG CCC ATC GCT                837
Ser Cys Asp Gly Leu Thr Ile Trp Glu Glu Arg Gly Arg Pro Ile Ala
                230                 235                 240

GGC AAG GGC CGA AAG GAG TCA GCG CAG CCC CCT GCC CAC CTT                        879
Gly Lys Gly Arg Lys Glu Ser Ala Gln Pro Pro Ala His Leu
                245                 250                 255

TGAGCAGGAC CTCACCTTGG CTCTGTTGCT GTCCTCCAGG GCGAGCACTT TCCACTTCCA              939

GAGGGGGCCA GAGGGACTTT GCCTGCCCAG TCTTTGGAGA GCTCAGTACA GGGCAGGAGC              999

TGCTGTGGTG TTCCCTTGGC AAATGAAAGT TTTATTTTCG TTTGGGAAAA AAAAAAAAA              1059

AAAAAAAAAA AAAAAAAAA A                                                       1080
```

( 2 ) INFORMATION FOR SEQ ID NO:2:

(i) SEQUENCE CHARACTERISTICS:
(A) LENGTH: 255 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

| Met | Thr | Cys | Gln | Ser | Cys | Val | Asp | Ala | Val | Arg | Lys | Ser | Leu | Gln | Gly |
|---|---|---|---|---|---|---|---|---|---|---|---|---|---|---|---|
| 1 | | | | 5 | | | | | 10 | | | | | 15 | |
| Val | Ala | Gly | Val | Gln | Asp | Val | Glu | Val | His | Leu | Glu | Asp | Gln | Met | Val |
| | | | 20 | | | | 25 | | | | | 30 | | | |
| Leu | Val | His | Thr | Thr | Leu | Pro | Ser | Gln | Glu | Val | Gln | Ala | Leu | Leu | Glu |
| | | | 35 | | | | 40 | | | | | 45 | | | |
| Gly | Thr | Gly | Arg | Gln | Ala | Val | Leu | Lys | Gly | Met | Gly | Ser | Gly | Gln | Leu |
| | | | 50 | | | | 55 | | | | | 60 | | | |
| Gln | Asn | Leu | Gly | Ala | Ala | Val | Ala | Ile | Leu | Gly | Gly | Ala | Gly | Thr | Val |
| 65 | | | | | 70 | | | | | 75 | | | | | 80 |
| Gln | Gly | Val | Val | Arg | Phe | Leu | Gln | Leu | Thr | Pro | Glu | Arg | Cys | Leu | Ile |
| | | | | 85 | | | | | 90 | | | | | 95 | |
| Glu | Gly | Thr | Ile | Asp | Gly | Leu | Glu | Pro | Gly | Leu | His | Gly | Leu | His | Val |
| | | | 100 | | | | 105 | | | | | 110 | | | |
| His | Gln | Tyr | Gly | Asp | Leu | Thr | Asn | Asn | Cys | Asn | Ser | Cys | Gly | Asn | His |
| | | | 115 | | | | 120 | | | | | 125 | | | |
| Phe | Asn | Pro | Asp | Gly | Ala | Ser | His | Gly | Gly | Pro | Gln | Asp | Ser | Asp | Arg |
| | 130 | | | | | 135 | | | | | 140 | | | | |
| His | Arg | Gly | Asp | Leu | Gly | Asn | Val | Arg | Ala | Asp | Ala | Asp | Gly | Arg | Ala |
| 145 | | | | | 150 | | | | | 155 | | | | | 160 |
| Ile | Phe | Arg | Met | Glu | Asp | Glu | Gln | Leu | Lys | Val | Trp | Asp | Val | Ile | Ala |
| | | | | 165 | | | | | 170 | | | | | 175 | |
| Arg | Ser | Leu | Ile | Ile | Asp | Glu | Gly | Glu | Asp | Asp | Leu | Gly | Arg | Gly | Gly |
| | | | | 180 | | | | | 185 | | | | | 190 | |
| His | Pro | Leu | Ser | Lys | Ile | Thr | Gly | Asn | Ser | Gly | Glu | Arg | Leu | Ala | Cys |
| | | | 195 | | | | 200 | | | | | 205 | | | |
| Gly | Ile | Ile | Ala | Arg | Ser | Ala | Gly | Leu | Phe | Gln | Asn | Pro | Lys | Gln | Ile |
| | 210 | | | | | 215 | | | | | 220 | | | | |
| Cys | Ser | Cys | Asp | Gly | Leu | Thr | Ile | Trp | Glu | Glu | Arg | Gly | Arg | Pro | Ile |
| 225 | | | | | 230 | | | | | 235 | | | | | 240 |
| Ala | Gly | Lys | Gly | Arg | Lys | Glu | Ser | Ala | Gln | Pro | Pro | Ala | His | Leu | |
| | | | | 245 | | | | | 250 | | | | | 255 | |

(2) INFORMATION FOR SEQ ID NO:3:

(i) SEQUENCE CHARACTERISTICS:
(A) LENGTH: 153 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

| Met | Lys | Ala | Val | Cys | Val | Met | Thr | Gly | Thr | Ala | Gly | Val | Lys | Gly | Val |
|---|---|---|---|---|---|---|---|---|---|---|---|---|---|---|---|
| 1 | | | | 5 | | | | | 10 | | | | | 15 | |
| Val | Lys | Phe | Thr | Gln | Glu | Thr | Asp | Asn | Gly | Pro | Val | His | Val | His | Ala |
| | | | 20 | | | | 25 | | | | | 30 | | | |
| Glu | Phe | Ser | Gly | Leu | Lys | Ala | Gly | Lys | His | Gly | Phe | His | Val | His | Glu |
| | | | 35 | | | | 40 | | | | | 45 | | | |

```
        Phe  Gly  Asp  Thr  Thr  Asn  Gly  Cys  Thr  Ser  Ala  Gly  Ala  His  Phe  Asn
             50                  55                       60

Pro  Thr  Lys  Gln  Glu  His  Gly  Ala  Pro  Glu  Asp  Ser  Ile  Arg  His  Val
        65                       70                  75                            80

Gly  Asp  Leu  Gly  Asn  Val  Val  Ala  Gly  Ala  Asp  Gly  Asn  Ala  Val  Tyr
                            85                       90                       95

Asn  Ala  Thr  Asp  Lys  Leu  Ile  Ser  Leu  Asn  Gly  Ser  His  Ser  Ile  Ile
                       100                      105                      110

Gly  Arg  Ser  Met  Val  Ile  His  Glu  Asn  Glu  Asp  Asp  Leu  Gly  Arg  Gly
                       115                      120                      125

Gly  His  Glu  Leu  Ser  Lys  Val  Thr  Gly  Asn  Ala  Gly  Gly  Arg  Leu  Ala
                  130                      135                      140

Cys  Gly  Val  Val  Gly  Leu  Ala  Ala  Glu
        145                      150
```

( 2 ) INFORMATION FOR SEQ ID NO:4:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
        Thr  Lys  Ala  Val  Cys  Val  Leu  Lys  Gly  Asp  Gly  Pro  Val  Gln  Gly  Thr
        1                   5                        10                       15

Ile  His  Phe  Glu  Ala  Lys  Gly  Asp  Thr  Val  Val  Val  Thr  Gly  Ser  Ile
                       20                       25                       30

Thr  Gly  Leu  Thr  Glu  Gly  Asp  His  Gly  Phe  His  Val  His  Gln  Phe  Gly
                       35                       40                       45

Asp  Asn  Thr  Gln  Gly  Cys  Thr  Ser  Ala  Gly  Pro  His  Phe  Asn  Pro  Leu
             50                       55                       60

Ser  Lys  Lys  His  Gly  Gly  Pro  Lys  Asp  Glu  Glu  Arg  His  Val  Gly  Asp
        65                       70                       75                       80

Leu  Gly  Asn  Val  Thr  Ala  Asp  Lys  Asn  Gly  Val  Ala  Ile  Val  Asp  Ile
                            85                       90                       95

Val  Asp  Pro  Leu  Ile  Ser  Leu  Ser  Gly  Glu  Tyr  Ser  Ile  Ile  Gly  Arg
                       100                      105                      110

Thr  Met  Val  Val  His  Glu  Lys  Pro  Asp  Asp  Leu  Gly  Arg  Gly  Gly  Asn
                       115                      120                      125

Glu  Glu  Ser  Thr  Lys  Thr  Gly  Asn  Ala  Gly  Ser  Arg  Leu  Ala  Cys  Gly
                  130                      135                      140

Val  Ile  Gly  Ile  Ile  Lys
        145                      150
```

( 2 ) INFORMATION FOR SEQ ID NO:5:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
        Ala  Lys  Gly  Val  Cys  Val  Leu  Asn  Ser  Ser  Glu  Gly  Val  Lys  Gly  Thr
        1                   5                        10                       15
```

```
Ile  Phe  Phe  Thr  His  Glu  Gly  Asn  Gly  Ala  Thr  Thr  Val  Thr  Gly  Thr
          20                      25                           30

Val  Ser  Gly  Leu  Arg  Pro  Gly  Leu  His  Gly  Phe  His  Val  His  Ala  Leu
          35                      40                           45

Gly  Asp  Asn  Thr  Asn  Gly  Cys  Met  Ser  Thr  Gly  Pro  His  Phe  Asn  Pro
     50                            55                      60

Asp  Gly  Lys  Thr  His  Gly  Ala  Pro  Glu  Asp  Ala  Asn  Arg  His  Ala  Gly
65                            70                      75                      80

Asp  Leu  Gly  Asn  Ile  Ile  Val  Gly  Asp  Asp  Gly  Thr  Ala  Thr  Phe  Thr
               85                            90                           95

Ile  Thr  Asp  Ser  Gln  Ile  Pro  Leu  Ser  Gly  Pro  Asn  Ser  Ile  Val  Gly
               100                      105                      110

Arg  Ala  Ile  Val  Val  His  Ala  Asp  Pro  Asp  Asp  Leu  Gly  Lys  Gly  Gly
          115                      120                      125

His  Glu  Leu  Ser  Leu  Ser  Thr  Gly  Asn  Ala  Gly  Gly  Arg  Val  Ala  Cys
     130                      135                      140

Gly  Ile  Ile  Gly  Ile  Gln  Gly
145                      150
```

( 2 ) INFORMATION FOR SEQ ID NO:6:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Val  Lys  Ala  Val  Cys  Val  Ile  Asn  Gly  Asp  Ala  Lys  Gly  Thr  Val  Phe
1                   5                      10                          15

Phe  Glu  Gln  Glu  Ser  Ser  Gly  Thr  Pro  Val  Lys  Val  Ser  Gly  Glu  Val
               20                      25                           30

Cys  Gly  Leu  Ala  Lys  Gly  Leu  His  Gly  Phe  His  Val  His  Glu  Phe  Gly
          35                      40                           45

Asp  Asn  Thr  Asn  Gly  Cys  Met  Ser  Ser  Gly  Pro  His  Phe  Asn  Pro  Tyr
     50                            55                      60

Gly  Lys  Glu  His  Gly  Ala  Pro  Val  Asp  Glu  Asn  Arg  His  Leu  Gly  Asp
65                            70                      75                      80

Leu  Gly  Asn  Ile  Glu  Ala  Thr  Gly  Asp  Cys  Pro  Thr  Lys  Val  Asn  Ile
               85                            90                           95

Thr  Asp  Ser  Lys  Ile  Thr  Leu  Phe  Gly  Ala  Asp  Ser  Ile  Ile  Gly  Arg
               100                     105                      110

Thr  Val  Val  Val  His  Ala  Asp  Ala  Asp  Asp  Leu  Gly  Gln  Gly  Gly  His
          115                      120                      125

Glu  Leu  Ser  Lys  Ser  Thr  Gly  Asn  Ala  Gly  Ala  Arg  Ile  Gly  Cys  Gly
     130                      135                      140

Val  Ile  Gly  Ile  Ile  Lys  Val
145                      150
```

( 2 ) INFORMATION FOR SEQ ID NO:7:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

| Thr | Lys | Ala | Val | Cys | Val | Leu | Lys | Gly | Asp | Gly | Pro | Val | Gln | Gly | Ile |
| 1 | | | | 5 | | | | | 10 | | | | | 15 | |

| Ile | Asn | Phe | Glu | Gln | Lys | Glu | Ser | Asn | Gly | Pro | Val | Lys | Val | Trp | Gly |
| | | | 20 | | | | | 25 | | | | | 30 | | |

| Ser | Ile | Lys | Gly | Leu | Thr | Glu | Gly | Leu | His | Gly | Phe | His | Val | His | Glu |
| | | 35 | | | | | 40 | | | | | 45 | | | |

| Phe | Gly | Asp | Asn | Thr | Ala | Gly | Cys | Thr | Ser | Ala | Gly | Pro | His | Phe | Asn |
| | 50 | | | | | 55 | | | | | 60 | | | | |

| Pro | Leu | Ser | Arg | Lys | His | Gly | Gly | Pro | Lys | Asp | Glu | Glu | Arg | His | Val |
| 65 | | | | | 70 | | | | 75 | | | | | | 80 |

| Gly | Asp | Leu | Gly | Asn | Val | Thr | Ala | Asp | Lys | Asp | Gly | Val | Ala | Asp | Val |
| | | | | 85 | | | | | 90 | | | | | 95 | |

| Ser | Ile | Glu | Asp | Ser | Val | Ile | Ser | Leu | Ser | Gly | Asp | His | Cys | Ile | Ile |
| | | | 100 | | | | | 105 | | | | | 110 | | |

| Gly | Arg | Thr | Leu | Val | Val | His | Glu | Lys | Ala | Asp | Asp | Leu | Gly | Lys | Gly |
| | | 115 | | | | | 120 | | | | | 125 | | | |

| Gly | Asn | Glu | Glu | Ser | Thr | Lys | Thr | Gly | Asn | Ala | Gly | Ser | Arg | Leu | Ala |
| | | 130 | | | | | 135 | | | | | 140 | | | |

| Cys | Gly | Val | Ile | Gly | Ile | Gln | | | | | | | | | |
| 145 | | | | | 150 | | | | | | | | | | |

( 2 ) INFORMATION FOR SEQ ID NO:8:

( i ) SEQUENCE CHARACTERISTICS:
( A ) LENGTH: 151 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

| Val | Lys | Ala | Val | Cys | Val | Leu | Asn | Ser | Ser | Glu | Gly | Val | Ser | Gly | Thr |
| 1 | | | | 5 | | | | | 10 | | | | | 15 | |

| Tyr | Leu | Phe | Thr | Gln | Val | Gly | Val | Ala | Pro | Thr | Thr | Val | Asn | Gly | Asn |
| | | | 20 | | | | | 25 | | | | | 30 | | |

| Ile | Ser | Gly | Leu | Lys | Pro | Gly | Leu | His | Gly | Phe | His | Val | His | Ala | Leu |
| | | 35 | | | | | 40 | | | | | 45 | | | |

| Gly | Asp | Asn | Thr | Asn | Gly | Cys | Met | Ser | Thr | Gly | Pro | His | Tyr | Asn | Pro |
| | 50 | | | | | 55 | | | | | 60 | | | | |

| Ala | Gly | Lys | Glu | His | Gly | Ala | Pro | Glu | Asp | Glu | Val | Arg | His | Val | Gly |
| 65 | | | | | 70 | | | | 75 | | | | | | 80 |

| Asp | Leu | Gly | Asn | Ile | Thr | Val | Gly | Glu | Asp | Gly | Thr | Ala | Ser | Phe | Thr |
| | | | | 85 | | | | | 90 | | | | | 95 | |

| Ile | Thr | Asp | Lys | Gln | Ile | Pro | Leu | Thr | Gly | Pro | Gln | Ser | Ile | Ile | Gly |
| | | | 100 | | | | | 105 | | | | | 110 | | |

| Arg | Ala | Val | Val | Val | His | Ala | Asp | Pro | Asp | Asp | Leu | Gly | Lys | Gly | Gly |
| | | 115 | | | | | 120 | | | | | 125 | | | |

| His | Glu | Leu | Ser | Lys | Ser | Thr | Gly | Asn | Ala | Gly | Gly | Arg | Ile | Ala | Cys |
| | | 130 | | | | | 135 | | | | | 140 | | | |

| Gly | Ile | Ile | Gly | Ile | Gln | Gly | | | | | | | | | |
| 145 | | | | | 150 | | | | | | | | | | |

( 2 ) INFORMATION FOR SEQ ID NO:9:

( i ) SEQUENCE CHARACTERISTICS:

(A) LENGTH: 150 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:9:

| Val | Lys | Ala | Val | Ala | Val | Leu | Ala | Gly | Thr | Asp | Val | Lys | Gly | Thr | Ile |
|---|---|---|---|---|---|---|---|---|---|---|---|---|---|---|---|
| 1 | | | | 5 | | | | | 10 | | | | | 15 | |
| Phe | Phe | Ser | Gln | Glu | Gly | Asp | Gly | Pro | Thr | Thr | Val | Thr | Gly | Ser | Ile |
| | | | 20 | | | | | 25 | | | | | 30 | | |
| Ser | Gly | Leu | Lys | Pro | Gly | Leu | His | Gly | Phe | His | Val | His | Ala | Leu | Gly |
| | | | 35 | | | | 40 | | | | | 45 | | | |
| Asp | Thr | Thr | Asn | Gly | Cys | Met | Ser | Thr | Gly | Pro | His | Phe | Asn | Pro | Val |
| | 50 | | | | | 55 | | | | | 60 | | | | |
| Gly | Lys | Glu | His | Gly | Ala | Pro | Glu | Asp | Glu | Asp | Arg | His | Ala | Gly | Asp |
| 65 | | | | | 70 | | | | | 75 | | | | | 80 |
| Leu | Gly | Asn | Val | Thr | Ala | Gly | Glu | Asp | Gly | Val | Val | Asn | Val | Asn | Ile |
| | | | | 85 | | | | | 90 | | | | | 95 | |
| Thr | Asp | Ser | Gln | Ile | Pro | Leu | Ala | Gly | Pro | His | Ser | Ile | Ile | Gly | Arg |
| | | | 100 | | | | | 105 | | | | | 110 | | |
| Ala | Val | Val | Val | His | Ala | Asp | Pro | Asp | Asp | Leu | Gly | Lys | Gly | Gly | His |
| | | | 115 | | | | 120 | | | | | 125 | | | |
| Glu | Leu | Ser | Lys | Ser | Thr | Gly | Asn | Ala | Gly | Gly | Arg | Val | Ala | Cys | Gly |
| | | | 130 | | | | | 135 | | | | | 140 | | |
| Ile | Ile | Gly | Ile | Gln | Gly | | | | | | | | | | |
| 145 | | | | | 150 | | | | | | | | | | |

(2) INFORMATION FOR SEQ ID NO:10:

(i) SEQUENCE CHARACTERISTICS:
(A) LENGTH: 151 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

| Met | Lys | Ala | Val | Cys | Val | Leu | Lys | Gly | Asp | Gly | Pro | Val | Gln | Gly | Thr |
|---|---|---|---|---|---|---|---|---|---|---|---|---|---|---|---|
| 1 | | | | 5 | | | | | 10 | | | | | 15 | |
| Ile | His | Phe | Glu | Gln | Lys | Ala | Ser | Gly | Glu | Pro | Trp | Leu | Ser | Gly | Gln |
| | | | 20 | | | | | 25 | | | | | 30 | | |
| Ile | Thr | Gly | Leu | Thr | Glu | Gly | Gln | His | Gly | Phe | His | Val | His | Gln | Tyr |
| | | | 35 | | | | | 40 | | | | | 45 | | |
| Gly | Asp | Asn | Thr | Gln | Gly | Cys | Thr | Ser | Ala | Gly | Pro | His | Phe | Asn | Pro |
| | 50 | | | | | 55 | | | | | 60 | | | | |
| His | Ser | Lys | Lys | His | Gly | Gly | Pro | Ala | Asp | Glu | Glu | Arg | His | Val | Gly |
| 65 | | | | | 70 | | | | | 75 | | | | | 80 |
| Asp | Leu | Gly | Asn | Val | Thr | Ala | Gly | Lys | Asp | Gly | Val | Ala | Asn | Val | Ser |
| | | | | 85 | | | | | 90 | | | | | 95 | |
| Ile | Glu | Asp | Arg | Val | Ile | Ser | Leu | Ser | Gly | Glu | His | Ser | Ile | Ile | Gly |
| | | | 100 | | | | | 105 | | | | | 110 | | |
| Arg | Thr | Met | Val | Val | His | Glu | Lys | Gln | Asp | Asp | Leu | Gly | Lys | Gly | Gly |
| | | | 115 | | | | | 120 | | | | | 125 | | |
| Asn | Glu | Glu | Ser | Thr | Lys | Thr | Gly | Asn | Ala | Gly | Ser | Arg | Leu | Ala | Cys |
| | | | 130 | | | | | 135 | | | | | 140 | | |
| Gly | Val | Ile | Gly | Ile | Ile | Gln | | | | | | | | | |

145 150

(2) INFORMATION FOR SEQ ID NO:11:

(i) SEQUENCE CHARACTERISTICS:
  (A) LENGTH: 150 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:11:

```
Val  Lys  Ala  Val  Cys  Val  Leu  Ala  Gly  Ser  Gly  Asp  Val  Lys  Val
 1                  5                        10                      15

Val  Arg  Phe  Glu  Gln  Gln  Asp  Asp  Gly  Asp  Val  Thr  Val  Glu  Gly  Lys
                20                       25                       30

Ile  Glu  Gly  Leu  Thr  Asp  Gly  Asn  His  Gly  Phe  His  Ile  His  Val  Phe
               35                       40                       45

Gly  Asp  Asn  Thr  Asn  Gly  Cys  Leu  Ser  Ala  Gly  Pro  His  Phe  Asn  Pro
          50                       55                       60

Gln  Asn  Lys  Asn  His  Gly  Ser  Pro  Lys  Asp  Ala  Asp  Arg  His  Val  Gly
 65                      70                       75                      80

Asp  Leu  Gly  Asn  Val  Thr  Ala  Glu  Gly  Gly  Val  Ala  Gln  Phe  Asn  Phe
                    85                       90                       95

Thr  Asp  Pro  Gln  Ile  Ser  Leu  Lys  Gly  Glu  Arg  Ser  Ile  Ile  Gly  Arg
               100                      105                      110

Thr  Ala  Val  Val  His  Glu  Lys  Gln  Asp  Asp  Leu  Gly  Lys  Gly  Gly  Asp
          115                      120                      125

Asp  Glu  Ser  Leu  Lys  Thr  Gly  Asn  Ala  Gly  Gly  Arg  Leu  Ala  Cys  Gly
     130                      135                      140

Val  Ile  Gly  Phe  Cys  Pro
145                      150
```

(2) INFORMATION FOR SEQ ID NO:12:

(i) SEQUENCE CHARACTERISTICS:
  (A) LENGTH: 152 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:12:

```
Val  Gln  Ala  Val  Ala  Val  Leu  Lys  Gly  Asp  Ala  Gly  Val  Ser  Gly  Val
 1                  5                        10                      15

Val  Lys  Phe  Glu  Gln  Ala  Ser  Glu  Ser  Glu  Pro  Thr  Thr  Val  Ser  Tyr
                20                       25                       30

Glu  Ile  Ala  Gly  Asn  Ser  Pro  Asn  Ala  Glu  Arg  Phe  His  Ile  His  Glu
               35                       40                       45

Phe  Gly  Asp  Ala  Thr  Asn  Gly  Cys  Val  Ser  Ala  Gly  Pro  His  Phe  Asn
     50                       55                       60

Pro  Phe  Lys  Lys  Thr  His  Gly  Ala  Pro  Thr  Asp  Glu  Val  Arg  His  Val
 65                      70                       75                      80

Gly  Asp  Met  Gly  Asn  Val  Lys  Thr  Asp  Glu  Asn  Gly  Val  Ala  Lys  Gly
                    85                       90                       95

Ser  Phe  Lys  Asp  Ser  Leu  Ile  Lys  Leu  Ile  Gly  Pro  Thr  Ser  Val  Val
               100                      105                      110

Gly  Arg  Ser  Val  Val  Ile  His  Ala  Gly  Gln  Asp  Asp  Leu  Gly  Lys  Gly
```

```
                        115                              120                              125
        Asp  Thr  Glu  Glu  Ser  Leu  Lys  Thr  Gly  Asn  Ala  Gly  Pro  Arg  Pro  Ala
             130                          135                    140

Cys  Gly  Val  Ile  Gly  Ile  Thr  Asn
        145                      150
```

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:13:

```
CGGGATCCAT  GGGCAGCGGC  CAGTTG                                                       26
```

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:14:

```
CGTCTAGAGG  TCCTGCTCAA  AGGTGGG                                                      27
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:15:

```
AATTAACCCT  CACTAAAGGG                                                               20
```

(2) INFORMATION FOR SEQ ID NO:16:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:16:

```
CGCTCTAGAT  CAAGCGTAGT  CTGGACGTC  GTATGGGTAA  AGGTGGGCAG  GGGGCTG                  57
```